United States Patent [19]

Takahashi et al.

[11] Patent Number: 5,058,567

[45] Date of Patent: * Oct. 22, 1991

[54] FLEXIBLE TUBE OF ENDOSCOPE AND METHOD OF AND APPARATUS FOR PRODUCING THE SAME

[75] Inventors: Nagashige Takahashi; Teruo Ouchi, both of Tokyo, Japan

[73] Assignee: Asahi Kogaku Kogyo Kabushiki Kaisha, Tokyo, Japan

[*] Notice: The portion of the term of this patent subsequent to Jul. 31, 2007 has been disclaimed.

[21] Appl. No.: 501,834

[22] Filed: Mar. 30, 1990

Related U.S. Application Data

[63] Continuation of Ser. No. 328,542, Mar. 24, 1989, Pat. No. 4,944,287.

[30] Foreign Application Priority Data

Mar. 29, 1988 [JP] Japan .................................. 63-77817
Mar. 29, 1988 [JP] Japan .................................. 63-77818
Apr. 8, 1988 [JP] Japan .................................. 63-87739

[51] Int. Cl.⁵ .............................................. A61B 1/00
[52] U.S. Cl. ...................................... 128/4; 420/401; 420/494
[58] Field of Search ........................................ 128/4, 6

[56] References Cited

U.S. PATENT DOCUMENTS

| 320,684 | 6/1885 | Platt | 228/128 |
| 4,295,672 | 10/1981 | Williams | 228/249 X |
| 4,646,722 | 3/1987 | Silverstein et al. | 128/4 |
| 4,753,222 | 6/1988 | Morishita | 128/4 |
| 4,805,292 | 2/1989 | Noguchi | 29/445 |
| 4,869,238 | 9/1989 | Opie et al. | 128/6 |
| 4,944,287 | 7/1990 | Takahashi et al. | 128/4 |

*Primary Examiner*—William H. Grieb
*Attorney, Agent, or Firm*—Sandler, Greenblum, & Bernstein

[57] ABSTRACT

An elongated flexible tube that constitutes an insert part of an endoscope. The flexible tube comprises: a spiral tube made of a precipitation hardening metal and having a groove which is recessed inwardly from the outer surface of the tube, the groove extending in a straight line along the axis of the tube, the spiral tube being subjected to age hardening process after a solid solution treatment; a braided-wire tube formed by weaving fine metal wires into a braid, the braided-wire tube being closely fitted over the outer surface of the spiral tube; and a flexible skin closely and watertightly fitted over the outer surface of the braided-wire tube.

5 Claims, 10 Drawing Sheets

FLEXIBLE TUBE OF ENDOSCOPE AND METHOD OF AND APPARATUS FOR PRODUCING THE SAME

This is a continuation of U.S. application Ser. No. 07/328,542 filed Mar. 24, 1989, now U.S. Pat. No. 4,944,287, issued on July 31, 1990.

BACKGROUND OF THE INVENTION

1. Field of the Invention

The present invention relates to a flexible tube that constitutes an insert part of an endoscope designed to be inserted into a hollow organ of the body or the like and also pertains to a method of and apparatus for producing the flexible tube More particularly, the present invention relates to a flexible tube of an endoscope which is designed so that a channel such as a biopsy, suction, air or water channel can be disposed along the outside of the flexible tube, and also pertains to a method of and apparatus for producing the flexible tube.

2. Description of the Related Art

The flexible tube of a typical conventional endoscope has heretofore been formed in the shape of an elongated tube having a circular cross-sectional configuration in such a manner that the outside of a spiral tube formed from a thin-walled, high-hardness stainless steel or phosphor bronze ribbon is covered with a braided-wire tube and the outside of the braided-wire tube is further covered with a flexible skin of a synthetic resin material.

In general endoscopes, channel tubes for biopsy and other channels are located inside the flexible tube. However, when it is desired to add second and third biopsy channels, an added biopsy channel must be located along the outside of the flexible tube. Further, there are cases where the channel tube is disposable in order to prevent transmission of bacteria and viruses from one patient to another through the endoscope. In such cases, the channel tube is located along the outside of the flexible tube.

However, since the flexible tube of the conventional endoscope has a simple circular cross-sectional configuration, if a channel tube is located along the outside of the flexible tube, the channel tube protrudes from the flexible tube and this prevents the flexible tube from being smoothly inserted into the patient's body and can inflict extra pain on the patient.

To overcome this problem, a U-shaped groove may be formed in the outer peripheral surface of the flexible tube along the axis thereof to receive a channel tube in the groove on the outer side thereof.

However, the flexible tubes of endoscopes need to be sufficiently strong to bear bending and crushing loads and, at the same time, must have high flexibility so that these tubes bend smoothly along the inner wall of a hollow organ of the patient's body. To meet the requirements, it is essential to employ a spiral tube made of a thin-walled, high-hardness material. However, it is not easy to form a U-shaped groove in a high-hardness material. If a U-shaped groove is axially formed in the outer surface of a spiral tube, the tube is likely to be twisted due to the residual strain or the like and it is therefore very difficult to form a U-shaped groove in a straight-line form.

It may be considered that the following press forming process is the best method of forming a U-shaped axial groove in the outer peripheral surface of a spiral tube, that is, a core bar which is formed with a groove (female die) having the same configuration as that of the desired U-shaped groove is inserted into a spiral tube and, in this state, the tube is pressed from the outer side thereof along the U-shaped groove in the core bar. In actual practice, however, such press forming process causes the spiral tube and the core bar to adhere to each other so strongly that the core bar cannot be removed from the spiral tube. Therefore, it is impossible with this method to produce a spiral tube having a U-shaped groove extending along the axis of the tube.

If the spiral tube is twisted, a kink is generated at every turn of the spiral, which causes the problem that an optical fiber bundle or the like is caught and damaged by such a kink. Due to these problems, it has heretofore been difficult to form a U-shaped groove for receiving a channel tube in the outer peripheral surface of a flexible tube in a straight line along the axis of the tube.

SUMMARY OF THE INVENTION

An object of the present invention is to provide a flexible tube of an endoscope which is designed so that it is possible to dispose a channel tube along the outer peripheral surface of the flexible tube without any protrusion, thereby enabling the flexible tube to be smoothly inserted into the patient's body without infliction of any extra pain on the patient.

It is a second object of the present invention to provide a method of producing a flexible tube of an endoscope which enables a flexible tube having a straight groove along the axis thereof to be formed so that the flexible tube has both strength and flexibility adequate for the insert part of an endoscope, and also provide an apparatus which may be effectively employed to carry out this method.

Other objects and advantages of the present invention will become apparent from the following detailed description of illustrated embodiments of the invention.

According to the present invention, there is provided an elongated flexible tube that constitutes an insert part of an endoscope, comprising: a spiral tube made of a precipitation hardening metal and having a groove which is recessed inwardly from the outer surface of the tube, the groove extending in a straight line along the axis of the tube, the spiral tube being subjected to age hardening process after a solid solution treatment; a braided-wire tube formed by weaving fine metal wires into a braid, the braided-wire tube being closely fitted over the outer surface of the spiral tube; and a flexible skin closely and watertightly fitted over the outer surface of the braided-wire tube.

In addition, there is provided a method of producing a flexible tube of an endoscope, comprising the steps of: covering the outer periphery of a spiral tube made of a precipitation hardening metal with a braided-wire tube formed by weaving fine wires of the same precipitation hardening metal as that for the spiral tube; forming a groove in the outer surface of the tube stock comprising the spiral tube and the braided-wire tube, the groove being recessed inwardly from the outer side of the tube stock and extending in a straight line along the axis of the tube stock; subjecting the tube stock to a solid solution treatment and then age hardening process; and watertightly coating a flexible skin on the outer surface of the braided-wire tube.

In addition, there is provided a method of producing a flexible tube of an endoscope, comprising the steps of: inserting a grooved core bar of a non-combustible material having a groove extending along the axis thereof into a metallic spiral tube formed so as to have a uniform diameter with a flexible thin-walled tubular member made of a combustible material being sandwiched therebetween; pressing the spiral tube against the groove in the core bar from the outer side thereof to form an axial groove in the spiral tube; and burning the thin-walled tubular member on heating and then removing the grooved core bar from the spiral tube.

In addition, there is provided a method of producing a flexible tube of an endoscope, comprising the steps of: longitudinally splitting a round bar having a groove extending in a straight line along the axis thereof into two halves along the center of the groove, and joining together the two halves of the round bar so as to be in contact with each other only at the bottom of the groove with a spacer being removably clamped between the opposing inner surfaces of the two halves, thereby forming a grooved core bar; inserting the grooved core bar into a spiral tube formed so as to have a uniform diameter over the entire length thereof; pressing the spiral tube from the outer side thereof against the groove in the core bar to form an axial groove in the spiral tube; and removing the spacer from the grooved core bar and then removing the grooved core bar from the spiral tube.

In addition, there is provided an apparatus for producing a flexible tube of an endoscope, comprising a split round bar having a groove extending in a straight line along the axis thereof, the round bar being longitudinally split into two halves along the center of the groove, the two halves being joined together so as to be in contact with each other only at the bottom of the groove; and a spacer removably clamped between the opposing inner surfaces of the two halves.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be now described in detail with reference to the accompanying drawings.

Figure 1:
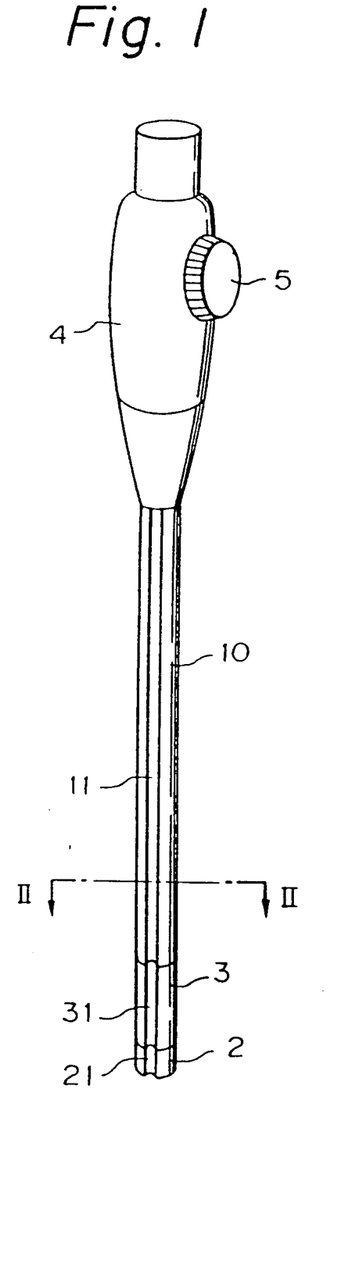
FIG. 1 is a perspective view showing the external appearance of an endoscope having a flexible tube according to the present invention attached thereto.

Referring first to FIG. 1, which shows the external appearance of an endoscope that employs a flexible tube 10 of one embodiment of the present invention, the reference numeral 2 denotes a distal end portion which incorporates an objective lens (not shown), and the numeral 3 denotes a bendable portion which is bendable by remote control. The reference numeral 4 denotes a control part which incorporates various control devices. A bending control knob 5 is rotatably provided on one side wall of the control part 4 for remote controlling the bending of the bendable portion 3.

The reference numeral 10 denotes an elongated flexible tube that constitutes an insert part of the endoscope, the flexible tube 10 connecting together the control part 4 and the bendable portion 3. A U-shaped groove 11 which is recessed inwardly is formed in the outer peripheral surface of the flexible tube 10 so as to extend in a straight line along the axis of the tube 10. Grooves 21 and 31 which are successively continuous with the U-shaped groove 11 are formed in the distal end portion 2 and the bendable portion 3, respectively.

Figure 2:
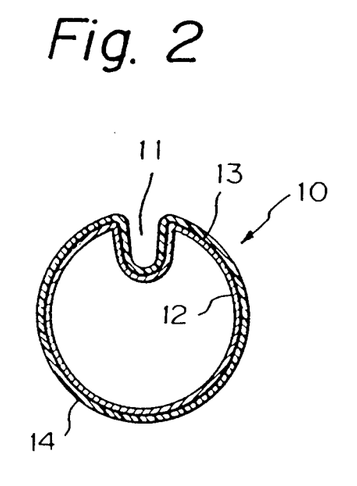
FIG. 2 is a sectional view taken along a section perpendicular to the axis of the flexible tube shown in FIG. 1.

FIG. 2 is a sectional view of the flexible tube 10. Although an optical fiber bundle and other associated elements are incorporated inside the flexible tube 10, illustration thereof is omitted. The flexible tube 10 is formed in such a manner that the outer side of a spiral tube 12 is closely covered with a braided-wire tube 13 formed by weaving fine metal wires into a braid and the outer surface of the braided-wire tube 13 is watertight and closely covered with a flexible skin 14 of a synthetic resin material. The spiral tube 12, the braided wire tube 13 and the skin 14 are all integrally recessed inwardly in the shape of a U in a sectional view, thus defining the above-described U-shaped groove 11.

Figure 3:
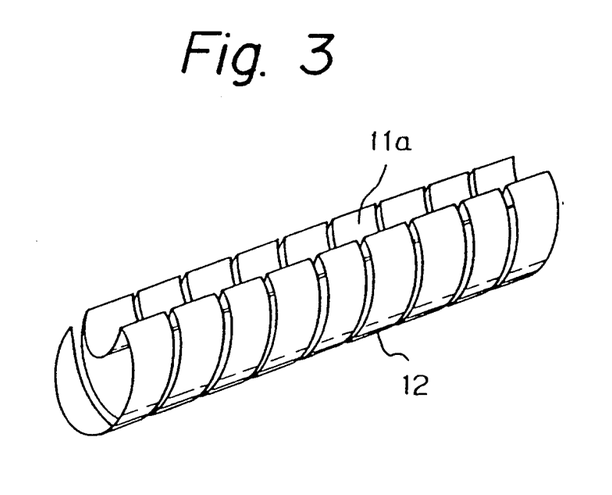
FIG. 3 is a perspective view of a spiral tube employed to form the flexible tube according to the present invention.

FIG. 3 is a perspective view of the spiral tube 12. The spiral tube 12 is formed using a precipitation hardening alloy material, for example, beryllium bronze (copper-beryllium alloy), in such a manner that a thin-walled strip of such a material with a uniform width is wound in the form of a spiral with a uniform diameter. After a U-shaped groove 11a has been formed therein, the spiral tube 12 is subjected to a solid solution treatment with a core bar, for example, inserted therein over the entire length thereof so that the spiral tube 12 will not be twisted due to the strain produced during the working process. After the residual strain has been removed by the treatment, the spiral tube 12 is hardened by an age hardening process.

Thus, since a precipitation hardening alloy material can be hardened in the final stage by age hardening, the U-shaped groove 11a can be readily formed by using a relatively soft material.

When beryllium bronze is employed as a material for the spiral tube 12, in the solid solution treatment, it is heated, for example, at 810° C. for 10 minutes or more and then quenched and in the age hardening process the material is held, for example, at 315° C. for 2 hours or more.

It should be noted that, since beryllium bronze is capable of shielding X-rays, the optical fiber bundle inserted in the spiral tube 12 can be protected to a certain extent from yellowing caused by irradiation with X-rays. However, any precipitation hardening alloy material may be employed in addition to beryllium bronze, for example, a precipitation hardening stainless steel alloy, a precipitation hardening duralumin alloy, etc.

Figure 4:
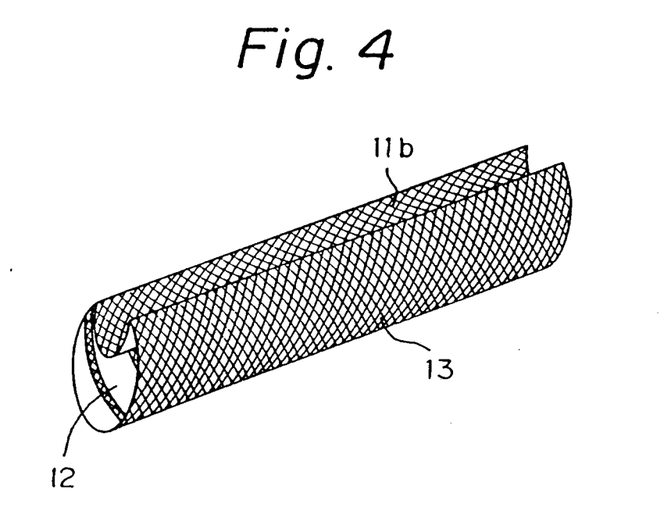
FIG. 4 is a perspective view of the spiral tube which is covered with a braided-wire tube.

FIG. 4 shows the spiral tube 12 closely covered with the braided-wire tube 13. The braided-wire tube 13 may be formed using ordinary stainless steel wires, but it is preferable to employ the same precipitation hardening alloy material as that for the spiral tube 12. From the viewpoint of the production process, it is preferable to form the U-shaped groove 11b shown in FIG. 4 in such a manner that the braided-wire tube 13 closely fits over the outer side of the spiral tube 12 which has not yet been formed with the U-shaped groove 11a and then the U-shaped groove 11b is formed in the integral structure that comprises the spiral tube 12 and the braided-wire tube 13.

If the U-shaped groove 11b is formed in this way, no noticeable twist is generated, but torsional stress remains in the spiral tube 12. The residual stress in the spiral tube 12 is relieved by the age hardening process. If the braided-wire tube 13 is formed using the same precipitation hardening alloy material as that for the spiral tube 12, the braided-wire tube 13 is subjected to the solid solution treatment and then subjected to age hardening, together with the spiral tube 12 in one unit.

Figure 5:
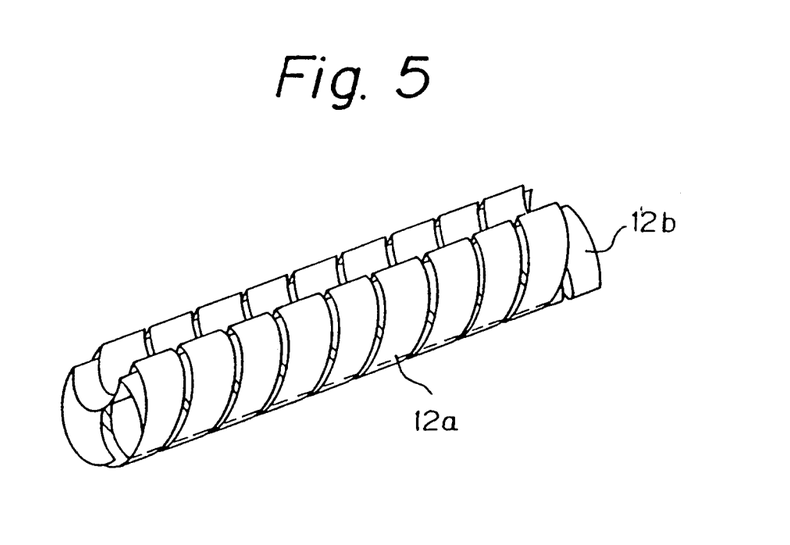
FIG. 5 is a perspective view of a double spiral tube formed from two spiral tube elements which are different from each other in the direction of spiral winding.

FIG. 5 shows a spiral tube formed in such a manner that a plurality of spiral tube elements 12a and 12b, which are different from each other in the direction of spiral winding, are closely fitted to each other to form a multilayer spiral tube. The material and heat treatment for this example are the same as those in the case of the spiral tube shown in FIG. 3. The arrangement shown in FIG. 5 enables an increase in the torsional strength. Thus, the spiral tube may have a multilayer structure.

Referring back to FIG. 2, the skin 14 that is fitted over the outside of the braided-wire tube 13 is formed using a synthetic resin material, for example, a polyurethane resin material. The skin 14 may be formed by coating a flexible plastic material on the outer surface of the braided-wire tube 13 by extrusion coating or other similar process. Alternatively, a skin which has been formed in the shape of a tube beforehand may be brought into close contact with the outer surface of the braided-wire tube 13 by thermal processing or a method utilizing evacuation.

Figure 6:
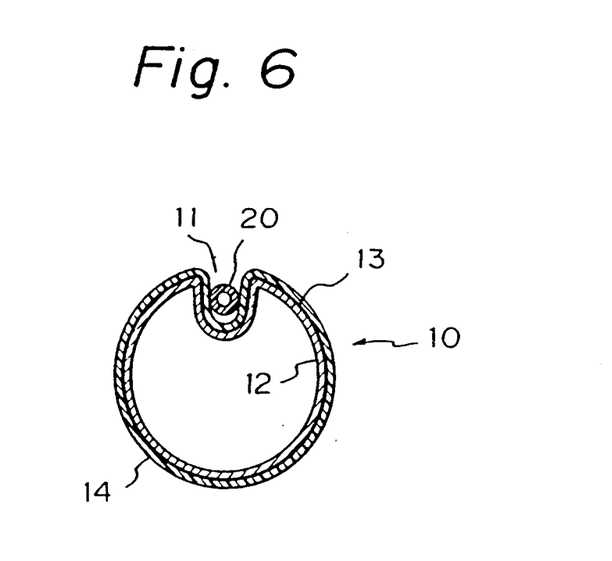
FIG. 6 is a sectional view of the flexible tube having a channel tube inserted in the U-shaped groove.

In the flexible tube of an endoscope according to this embodiment that is formed as described above, a U-shaped groove 11 is formed in a straight line along the axis of the tube, as shown in FIGS. 1 and 2, so that it is possible to accommodate a channel tube 20 for, for example, a biopsy channel, within the U-shaped groove 11, as shown in FIG. 6.

It should be noted that various processing conditions, e.g., the temperature and time for each heat treatment, may be appropriately changed in accordance with the composition and size of each material employed and are therefore not restricted to those shown in the above-described embodiment.

Thus, according to the present invention, the strain that is produced during the formation of a U-shaped groove in the spiral tube is removed by the solid solution treatment, so that it is possible to form a straight flexible tube of an endoscope which has neither twist nor kink. In addition, the spiral tube is hardened to impart adequate strength thereto by the age hardening process carried out thereafter and it is therefore possible to form a U-shaped groove with ease using a material which is relatively soft before the hardening process. As a result, a channel tube is received within the U-shaped groove in such a manner as to extend along the axis of the flexible tube without any protrusion, so that the flexible tube can be smoothly inserted into the patient's body without infliction of any extra pain to the patient. In addition, there is no fear that an optical fiber bundle and other associated elements inserted in the flexible tube will be caught and damaged in the flexible tube.

FIGS. 7 to 12 show in combination one embodiment of the method of producing a flexible tube of an endoscope according to the present invention.

Figure 7:
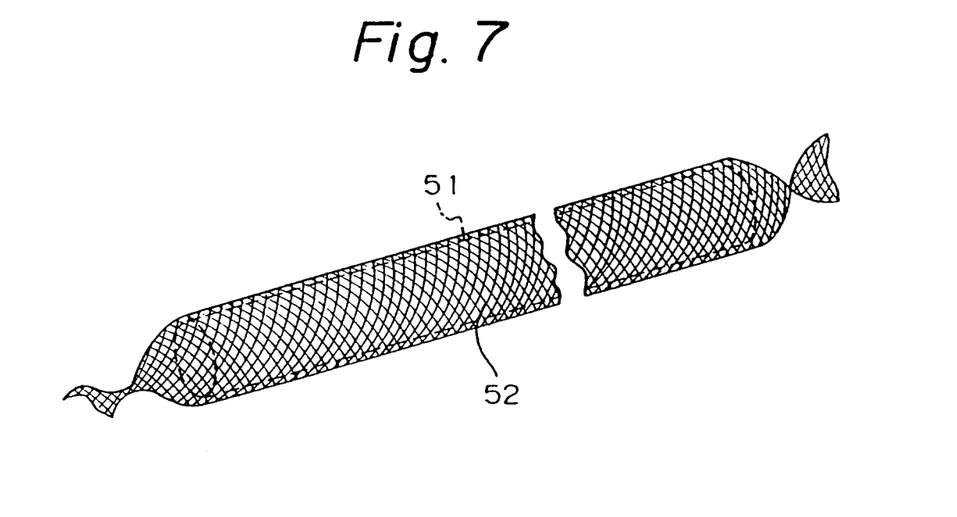
FIGS. 7 to 12 are perspective views showing the steps of one embodiment of the method of producing a flexible tube of an endoscope according to the present invention.

Referring first to FIG. 7, a round bar 51 is closely covered at its outside with a combustible braid 52 serving as a combustible thin-walled tubular member. The combustible braid 52 is flexible and therefore deformable. In this embodiment, it is formed using a material which evaporates or incinerates at a temperature on the order of 600° to 800° C., for example, silk thread, cotton thread or rayon. For the combustible braid 52, extrafine fibers, for example, those having a diameter of 0.1 mm or less, are employed. The outer diameter of the braid 52 is coincident with the inner diameter of a flexible tube which is to be produced. Accordingly, the outer diameter of the round bar 51 that is employed in this embodiment is equal to a value obtained by subtracting the wall thickness of the combustible braid 52 from the inner diameter of the flexible tube.

Figure 8:
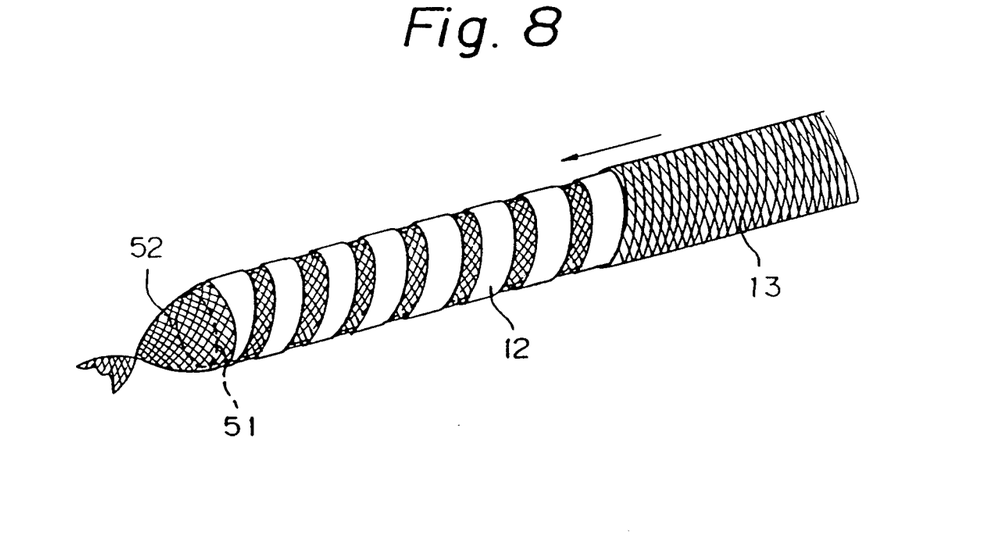

Next, the combustible braid 52 is inserted into a spiral tube 12 that constitutes a flexible tube of an endoscope, as shown in FIG. 8. The spiral tube 12 is formed by winding a thin-walled metallic strip with a uniform width into a spiral having a uniform diameter over the entire length thereof. The spiral tube 12 may be formed using a material which has superior strength and toughness, for example, a stainless steel or phosphor bronze. It is more preferable to employ a precipitation hardening alloy material, for example, beryllium bronze.

A braided-wire tube 13 is closely fitted over the outside of the spiral tube 12. The braided-wire tube 13 may be formed using fine stainless steel wires or the like. When a precipitation hardening alloy material is employed for the spiral tube 12, however, it is preferable to form the braided-wire tube 13 using the same alloy material as that for the spiral tube 12.

Figure 9:
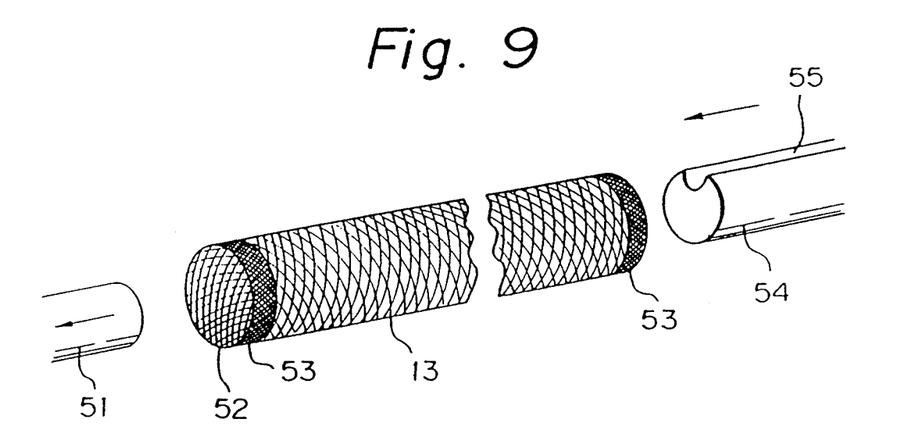

Next, as shown in FIG. 9, the spiral tube 12 and the braided-wire tube 13 are secured to each other at both axial end portions 53 by means of soldering. Thereafter, the tube stock comprising the tubes 12 and 13 is cut at the soldered portions 53 to cut off the outer portions of the soldered portions 53. The combustible braid 52 is bonded to the inner surfaces of the soldered portions 53 beforehand by means, for example, of a quick setting adhesive. Then, the round bar 51 is removed and a grooved core bar 54 made of a non-combustible high-hardness material is inserted instead. As a result, the combustible braid 52 is sandwiched between the spiral tube 12 and the grooved core bar 54. The grooved core bar 54 serves as a die (female die) used when a U-shaped groove is press-formed in the outer peripheral surface of the tube stock comprising the spiral tube 12 and the braided-wire tube 13 in the next step. The core bar 54 is, therefore, formed with a groove 55 having a U-shaped cross-sectional configuration and extending in a straight-line form.

Figure 10:
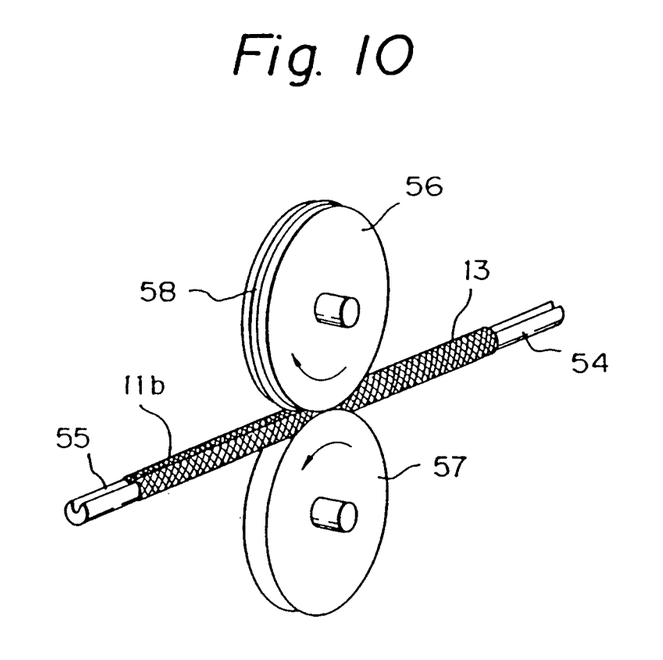
Figure 11:
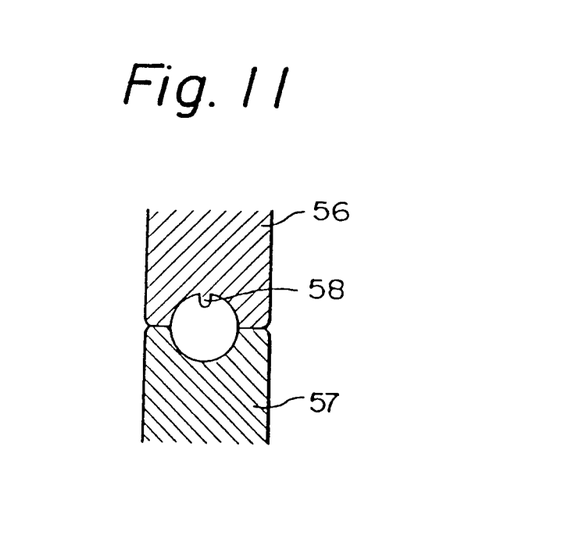

Next, the spiral tube 12 and the braided-wire tube 13 are simultaneously pressed against the U-shaped groove 55 in the core bar 54 to form a U-shaped groove extending along the axis of the tube stock. FIG. 10 shows one example of the press forming process. In this example, the tube stock comprising the spiral tube 12 and the braided-wire tube 13 is held between a pair of forming rolls 56 and 57 and, in this state, the rolls 56 and 57 are rotated. The respective outer peripheral surfaces of the forming rolls 56 and 57 are formed so as to define in combination the external shape of the braided-wire tube 13, as shown in FIG. 11. More specifically, one of the forming rolls, i.e., the roll 56, is provided with an elongated projection 58 around the entire circumference in conformity with the configuration of the U-shaped groove 55 in the core bar 54. The projection 58 serves as a male die used in the press forming process. Thus, a U-shaped groove 11b is formed in the outer peripheral surface of the tube stock comprising the spiral tube 12 and the braided-wire tube 13 along the axis of the tube stock. After the U-shaped groove 11b has been formed in this way, the combustible braid 52 is tightly clamped between the grooved core bar 54 and the spiral tube 12.

Figure 12:
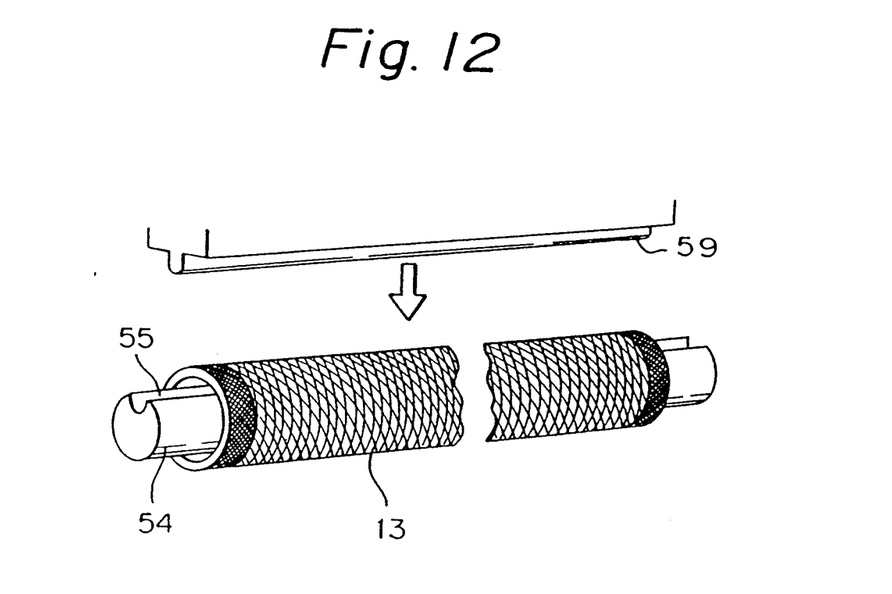

It should be noted that the above-described press forming process may also be conducted by an ordinary press working process, as shown in FIG. 12. The reference numeral 59 in the figure denotes an elongated projection serving as a male die.

The tube stock that has been formed with the U-shaped groove 11b is then heated. In the case where a precipitation hardening alloy material is employed for the spiral tube 12, the tube 12 is then subjected to a solid solution treatment. When beryllium bronze is employed as an alloy material, the solid solution treatment is carried out in such a manner that the alloy material is heated at 810° C. or more for 10 minutes or more and then quenched. By carrying out a solid solution treatment in this way, the strain produced during the press forming of the U-shaped groove 11b is removed and therefore the spiral tube 12 is not twisted. Thereafter, the spiral tube 12 is preferably subjected to age hardening by heating it, for example, at about 315° C. for 2 hours or more. Since a precipitation hardening alloy material such as beryllium bronze can be hardened in the final stage by age an hardening process, it is possible to form the U-shaped groove 11b with ease by using a relatively soft material.

The combustible braid 52 evaporates or incinerates when heated in the above-described process. As a result, a clearance corresponding to the thickness of the combustible braid 52 is generated between the grooved core bar 54 and the spiral tube 12. Therefore, the grooved core bar 54 can be readily removed from the spiral tube 12 at the end of the process.

It should be noted that, if heating is conducted in a vacuum furnace or a non-oxidizing atmosphere, it is possible to prevent oxidation of a spiral tube 12 made of an alloy material, e.g., beryllium bronze, and the grooved core bar 54. Moreover, the thin-walled tubular member (combustible braid 52) is burned up at the same time.

The spiral tube that is formed by the above-described method has the advantage that it is possible to conduct an operation such as soldering of the end faces of the tube without the need for pickling.

After the grooved core bar 54 has been removed, a skin 14 is coated on the outside of the braided-wire tube 13.

Thus, the method of producing a flexible tube of an endoscope according to the present invention enables the grooved core bar to be readily removed from the spiral tube after a U-shaped groove has been press-formed in the spiral tube and it is therefore possible to produce a flexible tube having a U-shaped groove formed in the outer peripheral surface along the axis thereof with ease using a spiral tube. Accordingly, it is possible to obtain a flexible tube with a U-shaped groove which has mechanical strength and flexibility adequate for practical use.

Since the thin-walled tubular member that is employed to provide a clearance between the spiral tube and the grooved core bar is deformable, it can cope with any kind of configuration of U-shaped groove. If extrafine fibers or the like are employed as the material for the thin-walled tubular member, the size of the clearance can be minimized and it is therefore possible to produce a flexible tube with a U-shaped groove with a high degree of accuracy.

It should be noted that the spiral tube may also be formed in such a manner that a plurality of spiral tube elements 12a and 12b which are different from each other in the direction of spiral winding are closely fitted to each other to form a multilayer spiral structure, as shown in FIG. 5. By doing so, the torsional strength of the spiral tube is enhanced. As the thin-walled tubular member, any thin-walled tubular material which is combustible and flexible may be employed. Various processing conditions such as the temperature and time for each heat treatment may be appropriately changed in accordance with the composition and size of each material employed.

FIGS. 13 to 21 show in combination another emdodiment of the method of producing a flexible tube of an endoscope according to the present invention and an apparatus which may be effectively employed to carry out the method of the present invention.

Figure 13:
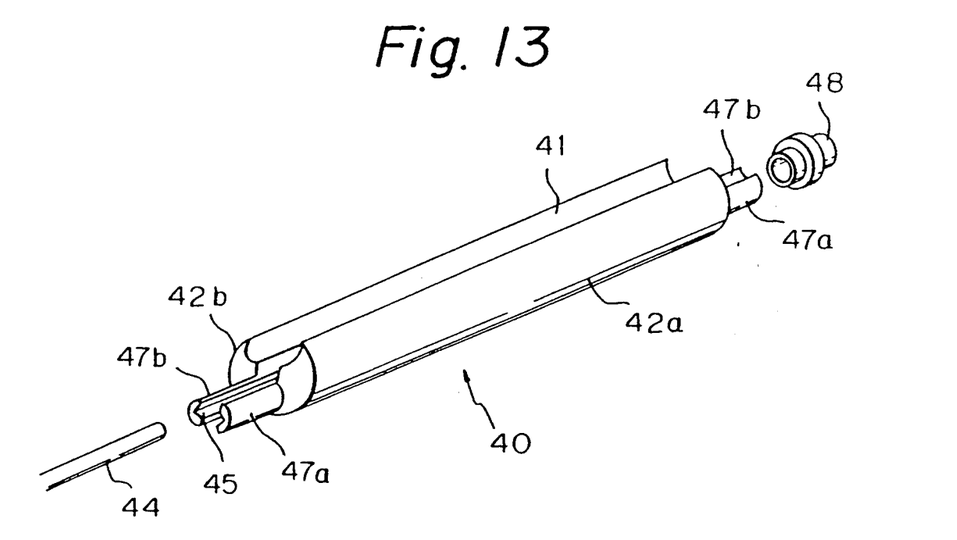
FIG. 13 is a perspective view of a grooved core bar which may be employed in the method of producing a flexible tube of an endoscope according to the present invention.
Figure 14:
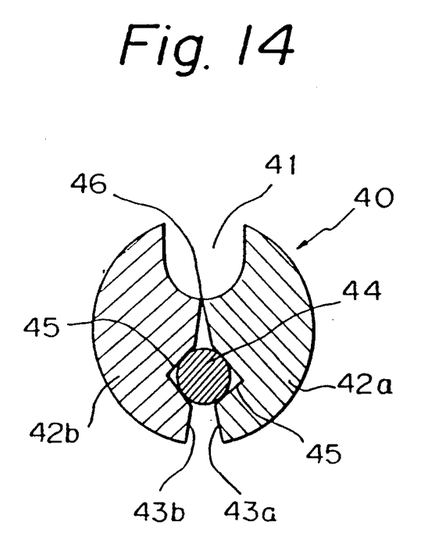
FIG. 14 is a sectional view of the grooved core bar.

Referring to FIG. 13, the reference numeral 40 denotes one example of a grooved core bar which may be employed in the present invention. The grooved core bar 40 comprises two core bar halves 42a and 42b which are formed by longitudinally splitting a round bar having a U-shaped groove 41 in the outer peripheral surface along the axis thereof in such a manner that the round bar is split along the center of the U-shaped groove 41. The core bar halves 42a and 42b are joined together with a spacer 44, for example, an elongated rod-shaped spacer, being removably clamped therebetween, thus forming a core bar as a whole. The opposing inner surfaces 43a and 43b of the core bar halves 42a and 42b are tapared so that the core bar halves 42a and 42b are in contact with each other only at the bottom 46 of the U-shaped groove 41, as shown in FIG. 14. Guide grooves 45 for guiding the spacer 44 are formed in the respective intermediate portions of the inner surfaces 43a and 43b in such a manner that the guide grooves 45 extend axially over the entire length of the core bar 40 in opposed relation to each other.

Figure 15:
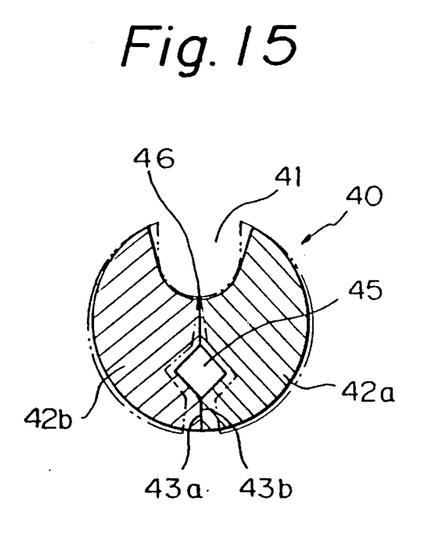
FIG. 15 is a sectional view of the grooved core bar with the spacer removed therefrom.

The spacer 44 can be inserted into and removed from the guide grooves 45 as desired. When the spacer 44 is removed from the guide grooves 45, it is possible to enlarge slightly the opening of the U-shaped groove 41 by pivoting the core bar halves 42a and 42b about the point of contact at the bottom 46 of the groove 41 until the inner surfaces 43a and 43b come into contact with each other.

Referring back to FIG. 13, the respective end portions of the core bar halves 42a and 42b are reduced in diameter so that only the portions surrounding the respective guide grooves 45 are left to define small-diameter portions 47a and 47b, and a ring 48 is fitted around the small-diameter portions 47a and 47b at each end. The ring 48 serves to retain temporarily the grooved core bar 40 at each end thereof so that the core bar 40 can not be disassembled. In FIG. 13, illustration of the ring at the left end is omitted.

Figure 16:
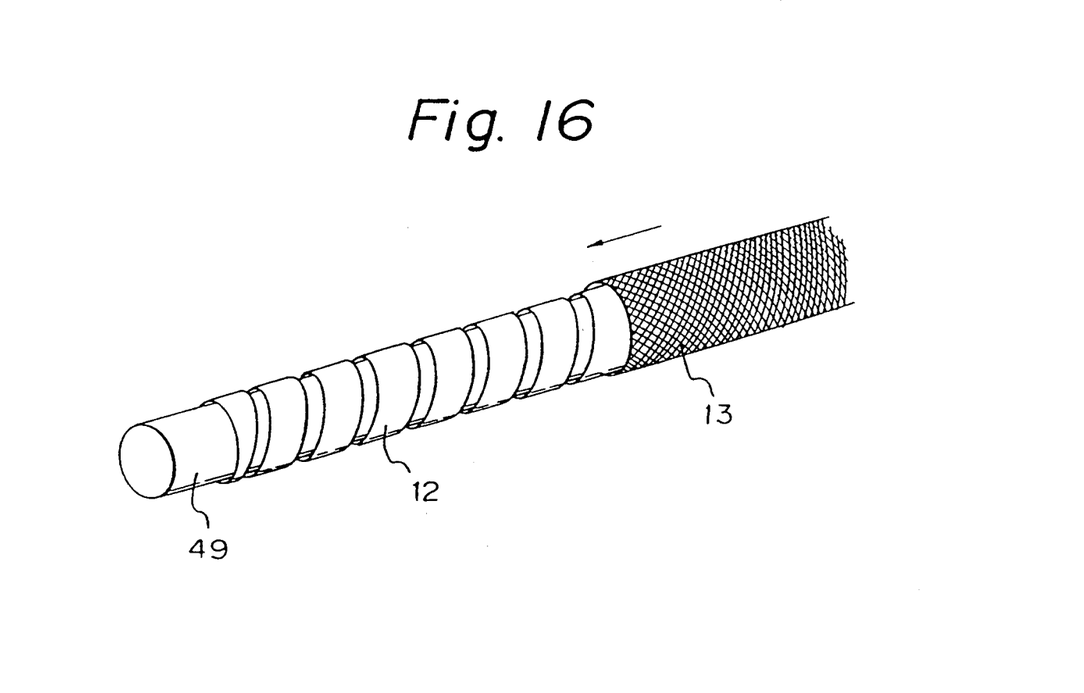
FIGS. 16 to 21 are perspective views showing the steps of another embodiment of the method of producing a flexible tube of an endoscope according to the present invention.

In production of a flexible tube, a braided-wire tube 13 is first tightly secured to the outside of a spiral tube 12, as shown in FIG. 16. This operation is conducted with a temporary core bar 49 in the form of a round bar being inserted in the spiral tube 12.

The spiral tube 12 is formed by winding a thin-walled metallic strip with a uniform width into a spiral having a uniform diameter over the entire length thereof. The spiral tube 12 may be formed using a material which has superior strength and toughness, for example, a stainless steel or phosphor bronze. It is preferable to employ a precipitation hardening alloy material, for example, beryllium bronze. The braided-wire tube 13 may be formed using fine stainless steel wires or the like. When a precipitation hardening alloy material is employed for the spiral tube 12, however, it is more preferable to form the braided-wire tube 13 using the same alloy material as that for the spiral tube 12.

Figure 17:
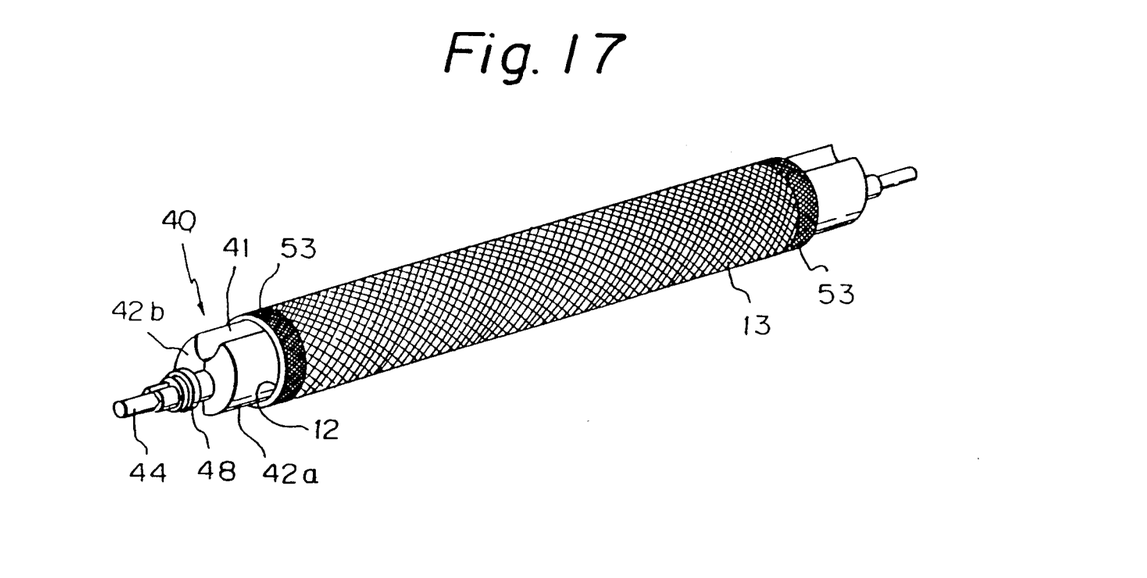

Next, the spiral tube 12 and the braided-wire tube 13 are secured to each other at both axial end portions 53 by means of soldering. Thereafter, the tube stock comprising the tubes 12 and 13 is cut at the soldered portions 53 to cut off the uneven outer portions of the soldered portions 53. Then, the temporary core bar 49 is removed and the grooved core bar 40 is inserted instead, as shown in FIG. 17. The grooved core bar 40 serves as a die (female die) used when a U-shaped groove is press-formed in the outer peripheral surface of the tube stock comprising the spiral tube 12 and the braided-wire tube 13 in the next step.

Figure 18:
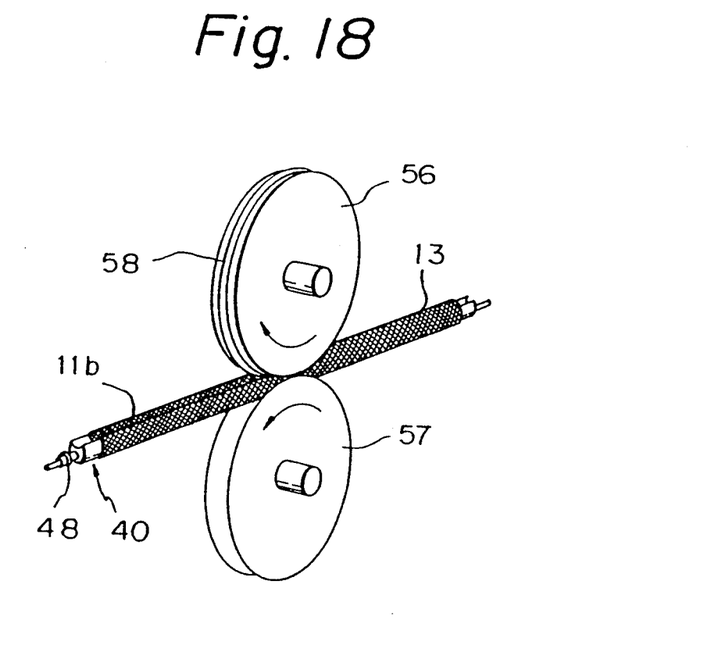
Figure 19:
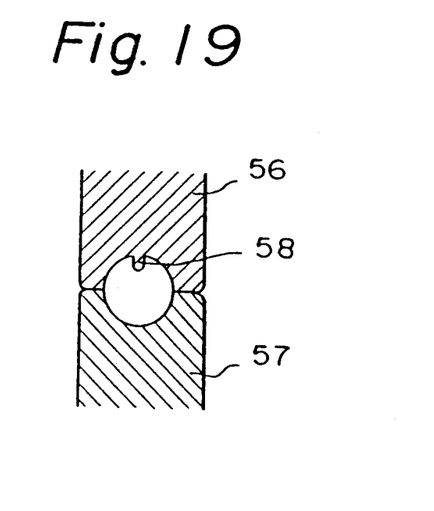

Next, the spiral tube 12 and the braided-wire tube 13 are simultaneously pressed against the U-shaped groove 41 in the core bar 40 to form a U-shaped groove extending along the axis of the tube stock. FIG. 18 shows one example of the press forming process. In this example, the tube stock comprising the spiral tube 12 and the braided-wire tube 13 is held between a pair of forming rolls 56 and 57 and, in this state, the rolls 56 and 57 are rotated. The respective outer peripheral surfaces of the forming rolls 56 and 57 are formed so as to define in combination the external shape of the braided-wire tube 13 as shown in FIG. 19. More specifically, one of the forming rolls, i.e., the roll 56, is provided with an elongated projection 58 around the entire circumference in conformity with the configuration of the U-shaped groove 41 in the core boar 40. The projection 58 serves as a male die used in the press forming process. Thus, a U-shaped groove 11b is formed in the outer peripheral surface of the tube stock comprising the spiral tube 12 and the braided-wire tube 13 along the axis of the tube stock.

Figure 20:
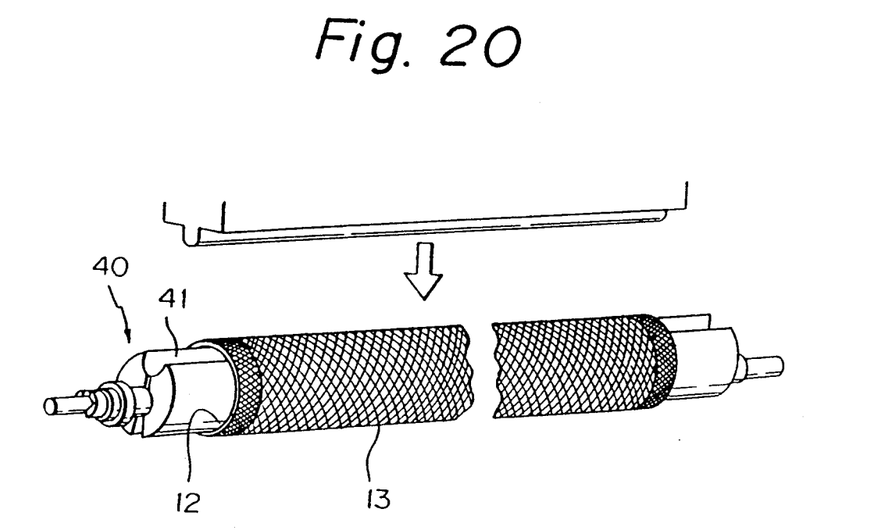

It should be noted that the above-described press forming process may also be conducted by an ordinary press working process, as shown in FIG. 20.

Figure 21:
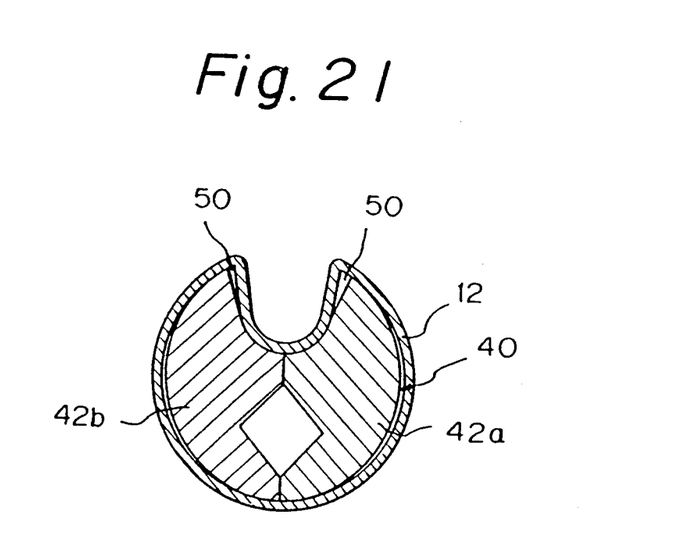

After the U-shaped groove 11b has been press-formed, the spacer 44 is removed from the grooved core bar 40 after the ring 48 has been removed. Then, the core bar halves 42a and 42b constituting the core bar 40 are pivoted about the point of contact at the bottom 46 of the U-shaped groove 41. Thus, the U-shaped groove 41 in the core bar 40 is slightly enlarged, resulting in a clearance 50 being produced between the spiral tube 12 and each side wall of the groove 41, as shown in FIG. 21. Thus, it is possible to remove the grooved core bar 40 from the spiral tube 12 with ease.

In the case where a precipitation hardening alloy material is employed for the spiral tube 12, the tube 12 is then subjected to a solid solution treatment. In such a case, a temporary core bar (not shown) formed from an inexpensive material, which has an external size which is slightly smaller than the internal size of the spiral tube 12, is inserted into the spiral tube 12, after the removal of the grooved core bar 40. When beryllium bronze is employed as an alloy material, the solid solution treatment is carried out in such a manner that the alloy material is heated at 810° C. or more for 10 minutes or more and then quenched. Thereafter, the spiral tube 12 is preferably subjected to age hardening by heating it, for example, at about 315° C. for 2 hours or more. Finally, a skin 14 is coated on the outside of the braided-wire tube 13.

Thus, the method of and apparatus for producing a flexible tube of an endoscope according to the present invention enable the grooved core bar to be readily removed from the spiral tube after a U-shaped groove has been press-formed in the spiral tube and it is therefore possible to produce a flexible tube having a U-shaped groove formed in the outer peripheral surface along the axis thereof with ease using a spiral tube. Accordingly, it is possible to obtain a flexible tube with a U-shaped groove which has mechanical strength and flexibility adequate for practical use.

It should be noted that the spiral tube may also be formed in such a manner that a plurality of spiral tube elements 12a and 12b which are different from each other in the direction of spiral winding are closely fitted to each other to form a multilayer spiral structure, as shown in FIG. 5. By doing so, the torsional strength of the spiral tube is enhanced.

The groove is not necessarily limited to a U-shaped groove but may have another cross-sectional configuration, for example, a V-shaped or rectangular cross-sectional configuration. The spacer may have any configuration, provided that it can be removably sandwiched between the core bar halves 42a and 42b that constitute the grooved core bar 40.

While the invention has been described by reference to specific embodiments chosen for purposes of illustration, it should be apparent that numerous modifications could be made thereto by those skilled in the art without departing from the basic concept and scope of the invention.

We claim:

1. An elongated flexible tube that constitutes an insert part of an endoscope, comprising:
a spiral rube having an outer surface with a periphery, and being made of a precipitation hardening metal and including a discontinuous portion in the periphery of the outer surface of said tube, said discontinuous portion extending along the axis of said tube, said spiral tube having been subjected to age hardening after a solid solution treatment;
a braided-wire tube formed by weaving fine metal wires into a braid, said braided-wire tube being closely fitted over the outer surface of said spiral tube.

2. A flexible tube of an endoscope according to claim 1, wherein said spiral tube is made of copper-beryllium alloy.

3. A flexible tube of an endoscope according to claim 1, wherein said braided-wire tube is made of the same precipitation hardening metal as that for said spiral tube.

4. A flexible tube of an endoscope according to claim 1, wherein said spiral tube comprises a plurality of spiral tube elements assembled together in close contact with each other, said spiral tube elements being different from each other in the direction of spiral winding.

5. A spiral tube for an elongated flexible tube that constitutes an insert part of an endoscope, said tube being made of a precipitation hardening metal and having a discontinuous portion in the periphery of said tube, said discontinuous portion extending in a straight line along the axis of said tube, said spiral tube having been subjected to age hardening after a solid solution treatment.

* * * * *

UNITED STATES PATENT AND TRADEMARK OFFICE
CERTIFICATE OF CORRECTION

PATENT NO. : 5,058,567

DATED : October 22, 1991

INVENTOR(S) : N. TAKAHASHI et al.

It is certified that error appears in the above-indentified patent and that said Letters Patent is hereby corrected as shown below:

At column 10, line 60 (claim 1, line 3) change "rube" to ---tube---.

Signed and Sealed this

Twenty-sixth Day of September, 1995

Attest:

BRUCE LEHMAN

Attesting Officer

Commissioner of Patents and Trademarks